(12) United States Patent
Gabriel et al.

(10) Patent No.: US 8,402,969 B2
(45) Date of Patent: Mar. 26, 2013

(54) METHOD FOR CONTROLLING A BI-LEVEL APPARATUS, AND BI-LEVEL APPARATUS

(76) Inventors: Stephan Gabriel, Dessau (DE); Ellis Whitehead, Freiburg (DE); Harald Genger, Dessau (DE)

(*) Notice: Subject to any disclaimer, the term of this patent is extended or adjusted under 35 U.S.C. 154(b) by 1005 days.

(21) Appl. No.: 11/526,487

(22) Filed: Sep. 25, 2006

(65) Prior Publication Data

US 2007/0089745 A1 Apr. 26, 2007

Related U.S. Application Data

(63) Continuation of application No. PCT/DE2005/000534, filed on Mar. 23, 2005.

(30) Foreign Application Priority Data

Mar. 23, 2004 (DE) .......................... 10 2004 014 538

(51) Int. Cl.
*A62B 7/04* (2006.01)

(52) U.S. Cl. ......... 128/204.23; 128/204.18; 128/204.21; 128/204.26

(58) Field of Classification Search ............. 128/204.23, 128/200.24, 204.18, 204.21, 204.25, 204.26, 128/204.28, 204.29, 205.11, 206.21
See application file for complete search history.

(56) References Cited

U.S. PATENT DOCUMENTS

| | | | | |
|---|---|---|---|---|
| 4,448,192 A * | 5/1984 | Stawitcke et al. | ........ | 128/204.26 |
| 5,433,193 A | 7/1995 | Sanders et al. | | |
| 5,494,028 A * | 2/1996 | DeVries et al. | .......... | 128/205.24 |
| 5,647,351 A * | 7/1997 | Weismann et al. | ...... | 128/204.21 |
| 5,865,173 A | 2/1999 | Froehlich | | |
| 6,345,619 B1 | 2/2002 | Finn | | |
| 6,626,174 B1 | 9/2003 | Genger et al. | | |
| 6,626,176 B1 | 9/2003 | Madaus et al. | | |
| 6,990,980 B2 * | 1/2006 | Richey, II | ............... | 128/204.26 |
| 7,000,612 B2 * | 2/2006 | Jafari et al. | .............. | 128/204.21 |
| 7,089,937 B2 * | 8/2006 | Berthon-Jones et al. | | 128/204.23 |
| 7,267,122 B2 * | 9/2007 | Hill | ........... | 128/204.23 |
| 2002/0185131 A1 | 12/2002 | Madaus et al. | | |
| 2003/0221689 A1 | 12/2003 | Berthon-Jones | | |
| 2005/0211249 A1 | 9/2005 | Wagner et al. | | |
| 2005/0217671 A1 * | 10/2005 | Fisher et al. | ............. | 128/204.18 |
| 2006/0027234 A1 * | 2/2006 | Gradon et al. | ........... | 128/204.21 |
| 2006/0102179 A1 * | 5/2006 | Rapoport et al. | ........ | 128/204.23 |
| 2006/0237015 A1 * | 10/2006 | Berthon-Jones et al. | | 128/204.23 |
| 2008/0283060 A1 * | 11/2008 | Bassin | ...................... | 128/204.18 |
| 2009/0038617 A1 * | 2/2009 | Berthon-Jones et al. | | 128/204.23 |

FOREIGN PATENT DOCUMENTS

| | | |
|---|---|---|
| DE | 19849571 A1 | 5/2000 |
| DE | 102 53 946 B3 | 1/2004 |
| EP | 0 656 216 | 6/1995 |
| EP | 1 005 829 | 6/2000 |
| WO | WO 98/35715 | 8/1998 |
| WO | WO 0010633 A1 * | 3/2000 |
| WO | 0024446 A1 | 5/2000 |
| WO | 0174430 A1 | 10/2001 |
| WO | 0200283 A1 | 1/2002 |
| WO | 02083221 A2 | 10/2002 |

* cited by examiner

*Primary Examiner* — Steven Douglas
*Assistant Examiner* — LaToya M Louis
(74) *Attorney, Agent, or Firm* — King & Schickli, PLLC (57) ABSTRACT

This invention relates to a method for controlling a bi-level apparatus. The method includes repeatedly measuring an airflow, choosing an expiration threshold value and choosing an inspiration threshold value. Switching to an inspiration mode takes place if the airflow is greater than the expiration threshold value in a comparison with the expiration threshold value. A switching back to the expiration mode takes place if the airflow is smaller than the inspiration threshold value in a comparison with the inspiration threshold value. Moreover, the invention relates to a bi-level apparatus for performing the method.

25 Claims, 8 Drawing Sheets

Fig. 8

METHOD FOR CONTROLLING A BI-LEVEL APPARATUS, AND BI-LEVEL APPARATUS

CROSS REFERENCE TO RELATED CO-PENDING APPLICATIONS

This application is a continuation of international application number PCT/DE2005/000534 (publication number: WO 2005/092414 A1) filed on Mar. 23, 2005 and entitled METHOD FOR CONTROL OF A BI-LEVEL DEVICE AND BI-LEVEL DEVICE and claims the benefit of the above-mentioned international application and the corresponding German national patent application number 10 2004 014 538.5 filed on Mar. 23, 2004 and entitled VERFAHREN ZUR STEUERUNG EINES BILEVEL-GERÄTS SOWIE BILEVEL-GERÄT the contents of which are expressly incorporated herein by reference.

FIELD OF THE INVENTION

The invention relates to a method for controlling a bi-level apparatus, and bi-level apparatus. Specifically, this invention relates to the reliable detection of inspiration and expiration despite the pressure fluctuations generated by the bi-level apparatus.

BACKGROUND OF THE INVENTION

Like the slightly less complex CPAP-apparatus, bi-level apparatus serve the pneumatic splinting of the respiratory tract to avoid obstructive respiratory troubles during sleep.

The CPAP (continuous positive airway pressure) therapy was developed for the treatment of apneas and is described in Chest. Volume No. 110, pages 1077-1088, October 1996 and in Sleep, Volume No. 19, pages 184-188. A CPAP-apparatus generates a positive overpressure up to approximately 30 mbar by means of a compressor or turbine and administers the same, preferably via a humidifier, via a hose and a nose mask, to the respiratory tract of the patient. This overpressure is to make sure that the upper respiratory tract remains fully opened during the whole night, so that no apneas disturbing the patient's sleep will occur (DE 198 49 571 A1). The required overpressure depends, inter alia, on the sleeping phase and the body position of the sleeping person.

Frequently, the overpressure is a nuisance to the patient. To adjust the overpressure as low as possible but as high as necessary, so-called auto-CPAP-apparatus (compare FIG. 1) were developed. Algorithms for the adjustment of an optimum overpressure are known, for example, from WO 00/24446 A1, WO 02/00283 A1 and WO 02/083221 A1. As compared to the less complex CPAP-apparatus, which measure the air pressure, auto-CPAP-apparatus additionally measure the airflow to the patient. During the processing of the airflow, maximums and minimums are searched for in the time derivative of the airflow, and the inspiration and expiration phases are determined on the basis of these extremes.

Another approach to make the pneumatic splinting for the patient as comfortable as possible relates to so-called bi-level apparatus. Bi-level apparatus support the respiration of the patient by administering a slightly higher pressure to the patient during the inspiration as compared to the expiration.

Due to the different pressures during the inspiration and the expiration bi-level apparatus require the determination of the inspiration and expiration phases. In the bi-level apparatus known from WO 98/35715 A1 and EP 0 656 216 A2 the time derivative of the airflow is compared with threshold values so as to make a distinction between inspiration and expiration. According to WO 98/35715 A1 this method used to be the common one in the prior art (bridging paragraph from page 1 to page 2).

In connection with bi-level apparatus it is technically difficult to exactly detect the transitions between inspiration and expiration by means of the airflow, because the pressure is to be changed exactly during these transitions. By changing the pressure, the air in the respiratory hose and the patient's lungs is slightly compressed or expanded, so that the airflow generated by the respiration is superimposed by an airflow generated by the pressure change. The airflow generated by the pressure change is now particularly high exactly at those times that are to be detected with exactness.

It is also problematical that a derivative acts like a high-pass filtering, which results in a roughening of the signal so that noise occurs more strongly. Due to the roughness of the signal the simple comparison with threshold values may provide incorrect results. In WO 02/083221 A2 the derivative is therefore combined with a low-pass filtering, which is called "estimation of the derivative". On the other hand, a low-pass filtering has the disadvantage that it delays the rise or fall of a signal.

It is desirable to detect the transition moments between inspiration and expiration more exactly and thus determine the inspiration and expiration phases more exactly.

SUMMARY OF THE INVENTION

According to an embodiment of the invention a method for controlling a bi-level apparatus is provided. The airflow is repeatedly measured thereby obtaining measured airflow values. An expiration and an inspiration threshold value are chosen. The airflow is repeatedly compared with the expiration threshold value during an expiration mode. Switching to an inspiration mode takes place if the airflow is greater than the expiration threshold value in a comparison with the expiration threshold value. The airflow is repeatedly compared with the inspiration threshold value during the inspiration mode. Switching to the expiration mode takes place, if the airflow is smaller than the inspiration threshold value in a comparison with the inspiration threshold value.

According to another embodiment of the invention a respiratory apparatus comprises a fan, a pressure sensor, a flow sensor and a processor. The pressure sensor determines an overpressure under which air is provided by the fan. The flow sensor measures an airflow. The processor is connected to the pressure sensor and the flow sensor. A pressure signal is fed from the pressure sensor and an airflow signal from the flow sensor to the processor. The processor stores a sequence of instructions and is suitable for executing the instructions. The processor repeatedly obtains measured airflow values from the airflow signal. The processor chooses an expiration threshold value and an inspiration threshold value. The processor repeatedly compares the airflow values with the expiration threshold value during an expiration mode. The processor switches to an inspiration mode if an airflow value is greater than the expiration threshold value in a comparison with the expiration threshold value The processor repeatedly compares the airflow values with the inspiration threshold value during the inspiration mode and switches to the expiration mode if an airflow value is smaller than the inspiration threshold value in a comparison with the inspiration threshold value. An advantage of comparing the airflow with threshold values is that a roughening of the airflow by a time derivative and a delay caused by the low-pass filtering are avoided.

The choosing of the minimum airflow during the preceding expiration phase as threshold value immediately after switching to an inspiration mode, and the choosing of the maximum airflow during the preceding inspiration phase as threshold value immediately after switching to an expiration mode prevent that a further switching to the other respiratory mode takes place too fast as a result of the airflow fluctuations inherent in the pressure change.

The additional comparison of the derivative of the airflow with different threshold values during the inspiration and expiration phases, too, prevents an undesired switching to the other respiratory mode.

To achieve a noise suppression, the measured airflow is initially subjected to a median filtering and then averaged prior to calculating the derivative of the airflow. The median filtering advantageously suppresses outliers. The combination of a median filtering over a few measured values and a subsequent averaging over double the number of measured values is an optimum compromise between calculation expenditure, filtering time and required averaging.

The additional inclusion of the actual pressure increases the reliability of the switching between inspiration and expiration mode. One aspect is here that no switching to the inspiration mode is to take place in the event of coughing or sneezing. The actual pressure hereby increases above the set pressure because the pressure control loop is too sluggish to compensate such fast pressure fluctuations. The other aspect is that a switching to the inspiration mode is to take place if the actual pressure is below the set pressure and the airflow has strongly increased in a third predetermined time interval.

The lowering of the threshold value for the airflow during the expiration shortly after switching to the expiration mode renders the method increasingly sensitive to a switching back to inspiration mode. This advantageously corresponds to the average duration of an expiration phase.

In a correspondingly advantageous manner the threshold value for the airflow is raised approximately proportionally to the current airflow during the inspiration until the current airflow has reached a maximum. Upon reaching the maximum, the threshold value is approximately kept constant.

BRIEF DESCRIPTION OF THE DRAWINGS

Preferred embodiments of the invention will be explained in more detail by means of the attached drawings below. In the drawings.

DETAILED DESCRIPTION OF THE INVENTION

Figure 1:
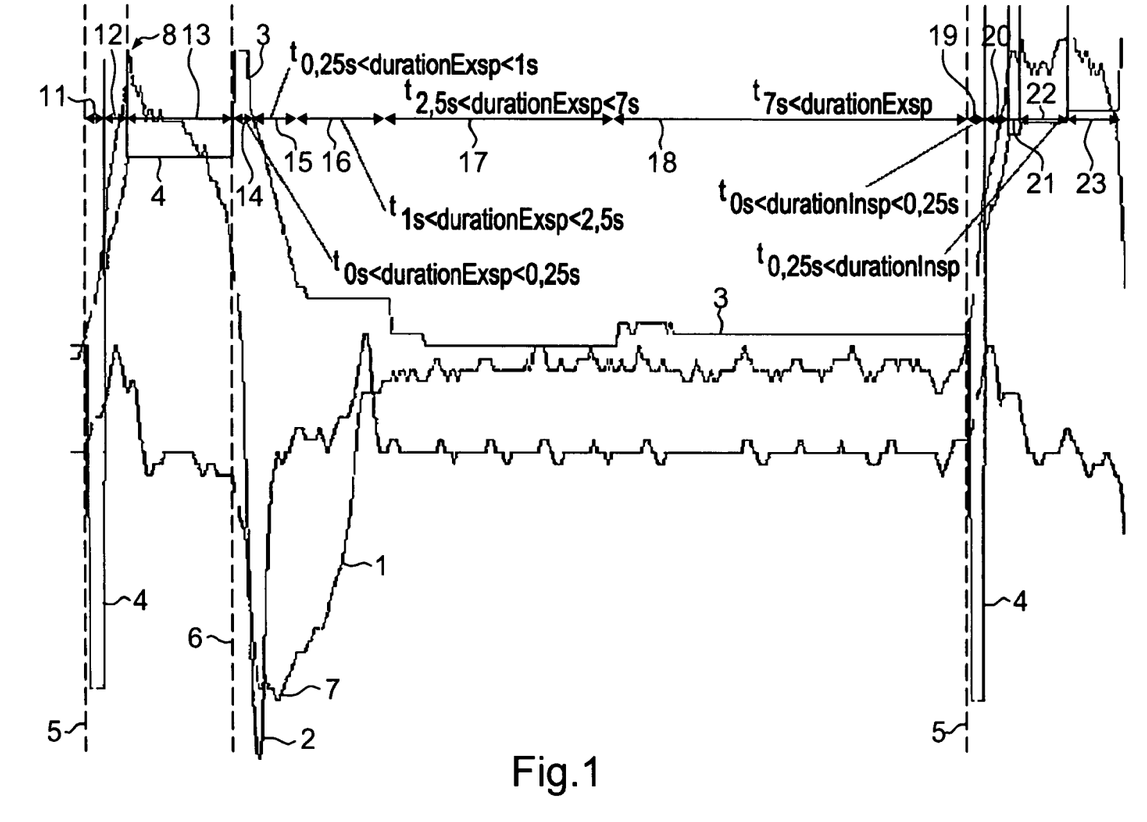
FIG. 1 shows a diagram depicting the timing of the airflow, the derivative of the airflow and the threshold value for the airflow.

FIG. 1 shows a diagram depicting the timing of the airflow 1, the derivative of the airflow 2 and the expiration threshold value 3 and the inspiration threshold value 4. Moreover, different time domains were marked, which will be explained in more detail below in connection with the flowchart of FIGS. 5 to 8. The expiration phase was intentionally dragged on by the test person in order to represent all time domains provided in the method according to the invention.

Figure 2:
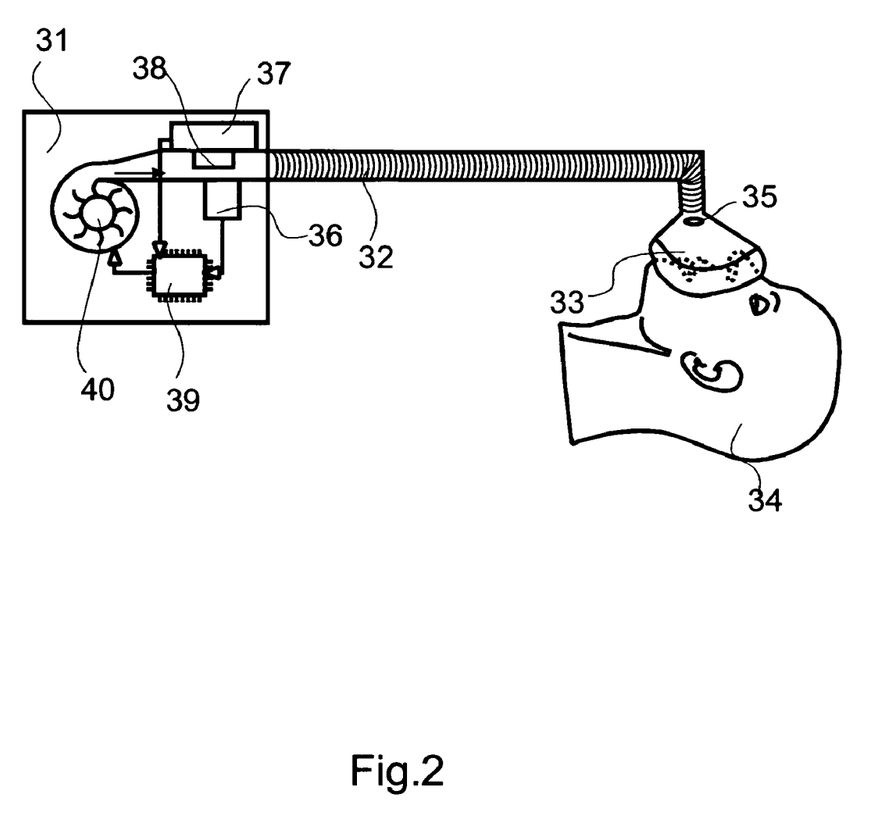
FIG. 2 shows the hardware of an auto-CPAP- or bi-level apparatus.

FIG. 2 schematically shows the hardware for an auto-CPAP- or a bi-level apparatus 31. A fan 40 conveys air and makes it available under an overpressure of up to 30 mbar. The air is administered to a patient 34 by means of a respiratory hose 32 and a mask 33. Air permanently escapes into the environment through the opening 35, so that exhaled air having a higher fraction of $CO_2$ is flushed out of the opening 35. A pressure sensor 36 for measuring the overpressure generated by the fan 40 is mounted in the apparatus 31. This overpressure will hereinafter be referred to as actual pressure. Moreover, the apparatus 31 comprises a flow sensor 37 for detecting the airflow. A heating wire 38 of the flow sensor 37 is depicted exemplarily. The signals provided by the flow sensor 37 and the pressure sensor 36 are fed to a microprocessor 39. The microprocessor, again, controls the speed of the fan 40.

The architecture of apparatus 31 follows the trend in the field of electronics to digitalize sensor signals as fast as possible and then to perform the signal processing digitally. The program executed by the microprocessor 39 includes an internal control loop according to which the speed of the fan is controlled such that the actual pressure measured by the pressure sensor 36 corresponds to a set pressure as well as possible. The set pressure is predetermined by other program parts. If the set pressure is predetermined without taking into account the inspiration and the expiration the apparatus 31 is a CPAP-apparatus. If, in addition, the airflow is evaluated to optimize the set pressure an auto-CPAP-apparatus is concerned. If different set pressures for inspiration and expiration are predetermined the apparatus 31 is a bi-level apparatus. Thus, it is merely a question of the other program parts whether the apparatus 31 works as an auto-CPAP- or as a bi-level apparatus.

Figure 3:
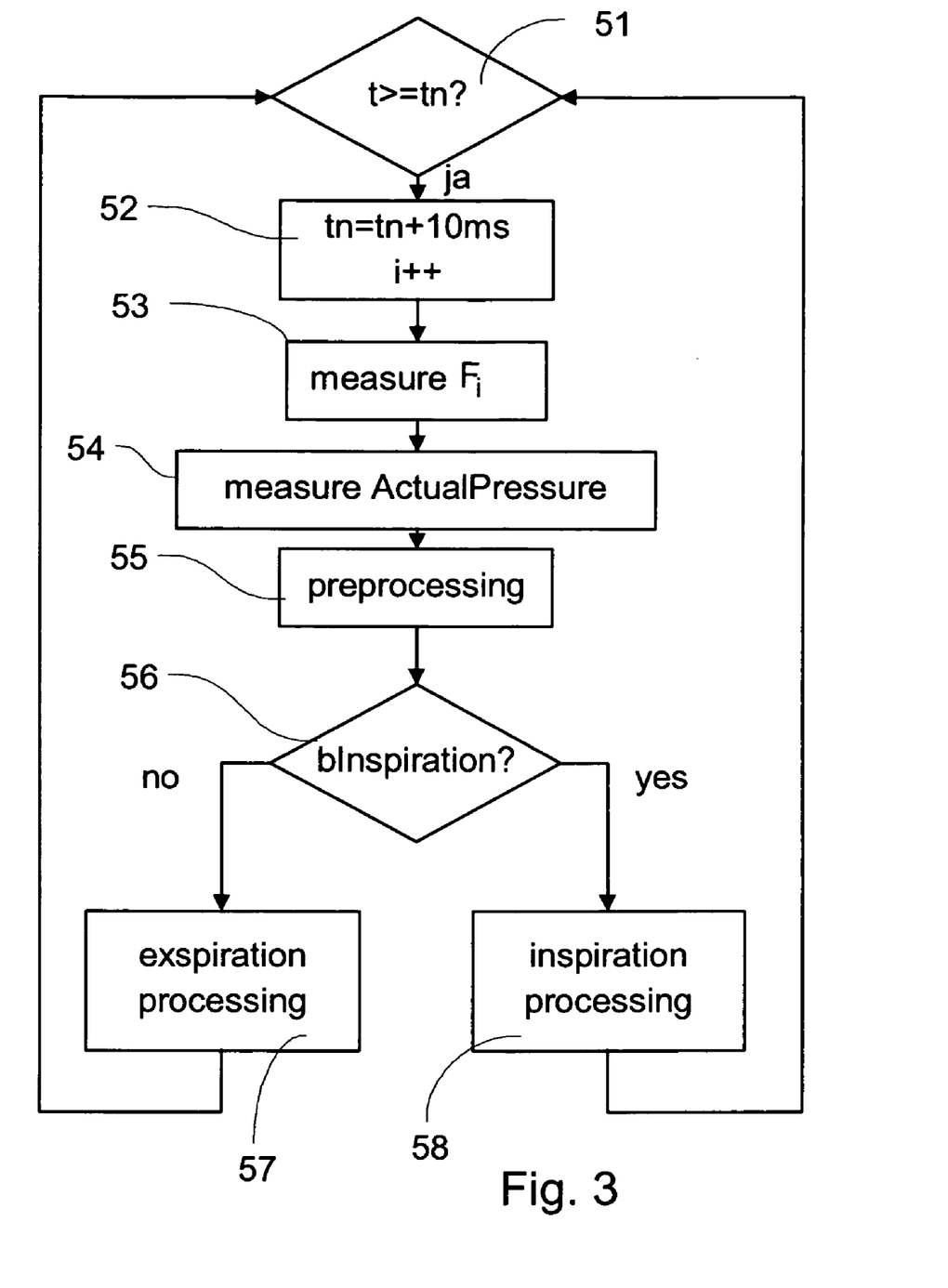
FIG. 3 shows a flowchart of the inventive control method for a bi-level apparatus.

FIG. 3 shows a flowchart of the method according to the invention. According to one embodiment the airflow $F_i$ is measured every 10 ms in step 53 and the actual pressure ActualPressure in step 54. The index i stands for the current airflow. As the set pressure is evaluated with less intensity than the airflow, an index for the set pressure seemed dispensable. The current time is designated with t. tn designates the time at which the next measurement is to take place. In step 51 it is waited until the next measuring time tn is reached. In step 52 tn is increased by 10 ms and i by 1.

A preprocessing takes place in step 55, which will be explained in more detail by means of FIG. 4. In step 56 it is verified whether the method is in an inspiration or expiration mode. Then, the Boolean variable bInspiration is true or false, respectively. The expiration processing 57 is performed in the expiration mode and then, in step 51, the next measuring time tn is awaited. The inspiration processing 58 is performed in the inspiration mode and then, in step 51, it is waited.

Figure 4:
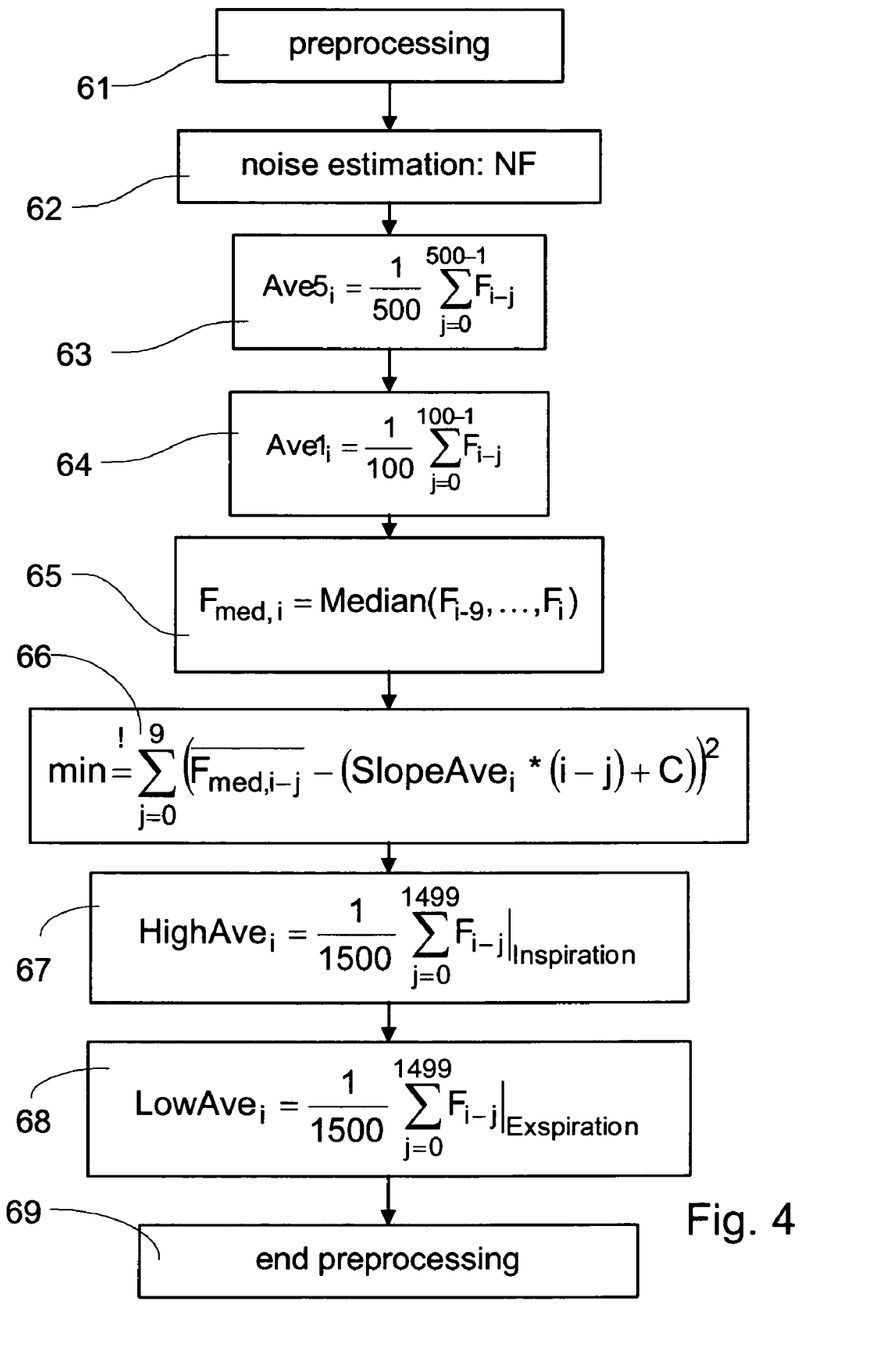
FIG. 4 shows a detailed flowchart for the preprocessing.

The preprocessing 55 is shown in more detail in FIG. 4. First, a noise estimation is made in step 62. The result is stored in variable NF (for "noise flow"). In a simple case, the noise estimation can take place during the development of the apparatus. In this case a constant value is stored in the variable NF. In a more complex embodiment the standard deviation of the measured airflow values $F_i$ from a specific time interval can be stored in the variable NF. The calculation of the standard deviation may be repeated from time to time, or may be made movingly for each i. Advantageously, a time interval is chosen in which the derivative of the airflow is as close as possible to zero. This is the case shortly after the apparatus has been switched on or in the middle of an inspiration or expiration phase.

In step 63 a first moving average value $Ave5_i$ (Ave=average) over the last 500 measured airflow values $F_i$ is calculated according to formula (1). This corresponds to an averaging of the air flow over five seconds.

$$Ave5_i = \frac{1}{500} \sum_{j=0}^{500-1} F_{i-j} \qquad (1)$$

Similarly, in step 64, another moving average value $Ave1_i$ is calculated from the 100 airflow values measured in the last second according to formula (2):

$$Ave1_i = \frac{1}{100} \sum_{j=0}^{100-1} F_{i-j} \qquad (2)$$

In step 65 a median filtering over the last ten measured airflow values is performed in accordance with formula (3). In a median filtering the average value or the arithmetic average of both average values is returned or processed further. A median filtering is more complicated than an average value calculation. However, the result is practically not affected by outliers, while outliers occur in the calculation of the average value.

$$F_{med,i} = \text{Median}(F_{i-9} \ldots, F_i) \qquad (3)$$

Then, a moving average value $\overline{F_{med,i}}$ is calculated over 20 median-filtered values $F_{med,i}$ in step 66. From the moving average value $\overline{F_{med,i}}$ the time derivative of the airflow SlopeAve$_i$ is estimated. In a simple case this may be accomplished by calculating SlopeAve$_i$ as slope of a straight line by two moving average values $\overline{F_{med,i}}$ and $\overline{F_{med,i-k}}$, which are apart from each other by k*10 ms. k can be, for example, 20. In another embodiment a straight line may be adapted to ten successive moving average values $\overline{F_{med,i}}$ according to formula (4), thereby minimizing the squares of error. The slope of this straight line SlopeAve$_i$ is interpreted as estimated airflow derivative. In another embodiment also the absolute errors can be minimized.

$$\min \stackrel{!}{=} \sum_{j=0}^{9} (\overline{F_{med,i-j}} - (SlopeAve_i * (i-j) + C))^2 \qquad (4)$$

Finally, in steps 67 and 68, another two moving average values HighAve$_i$ and LowAve$_i$ respectively are calculated over 1500 measured airflow values $F_i$ each in accordance with formula (5) or (6) respectively, which corresponds to a time span of 15 seconds. The special thing about these averagings is that only airflow values $F_i$ measured during the inspiration are included in HighAve$_i$ and that only airflow values $F_i$ measured during the expiration are included in LowAve$_i$. If the variable bInspiration is true, the method according to the invention is in the inspiration mode, so that the measured airflow values $F_i$ are used to calculate HighAve$_i$. Otherwise, the method is in the expiration mode, so that the measured airflow values $F_i$ are used to calculate LowAve$_i$.

$$HighAve_i = \frac{1}{1500} \sum_{j=0}^{1499} F_{i-j}|_{Inspiration} \qquad (5)$$

$$LowAve_i = \frac{1}{1500} \sum_{j=0}^{1499} F_{i-j}|_{Expiration} \qquad (6)$$

Figure 5:
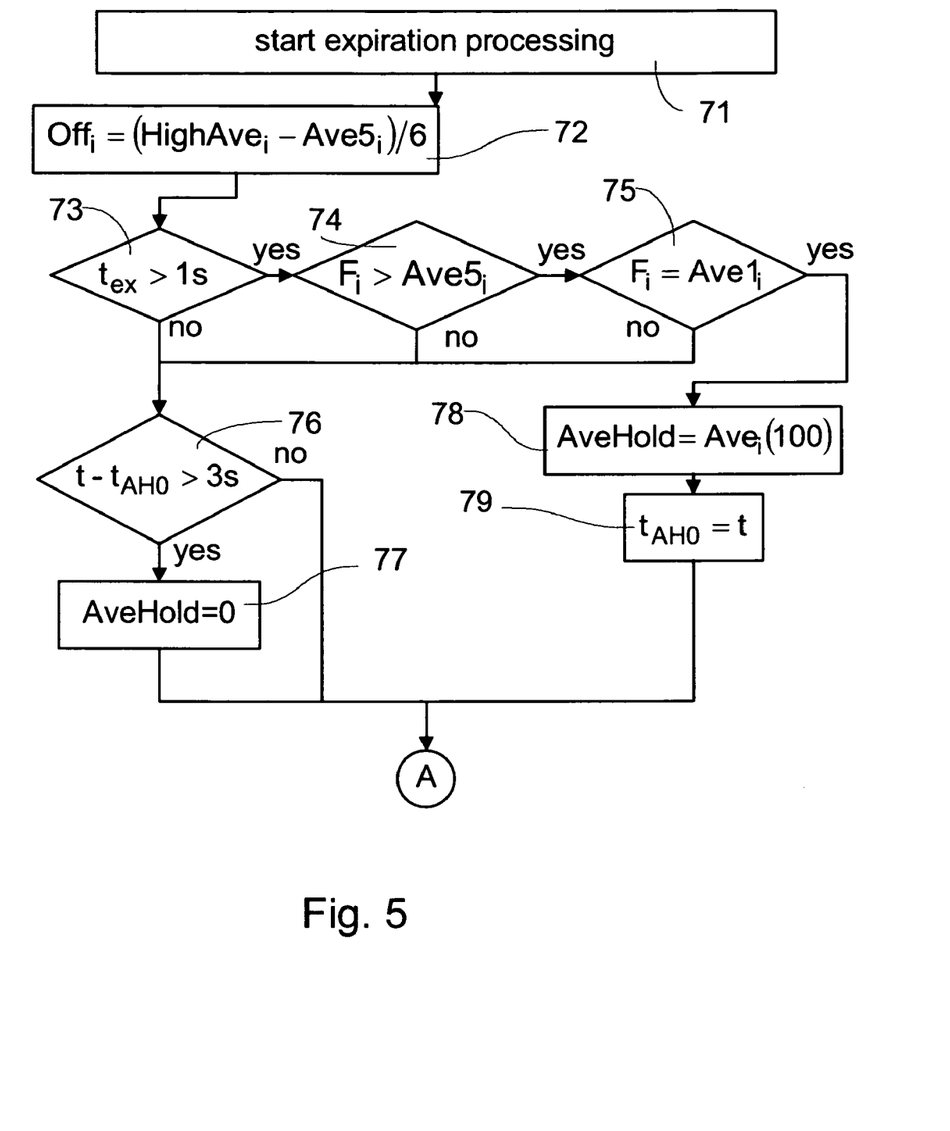
FIG. 5 to 7 show a detailed flowchart for the expiration processing.
Figure 6:
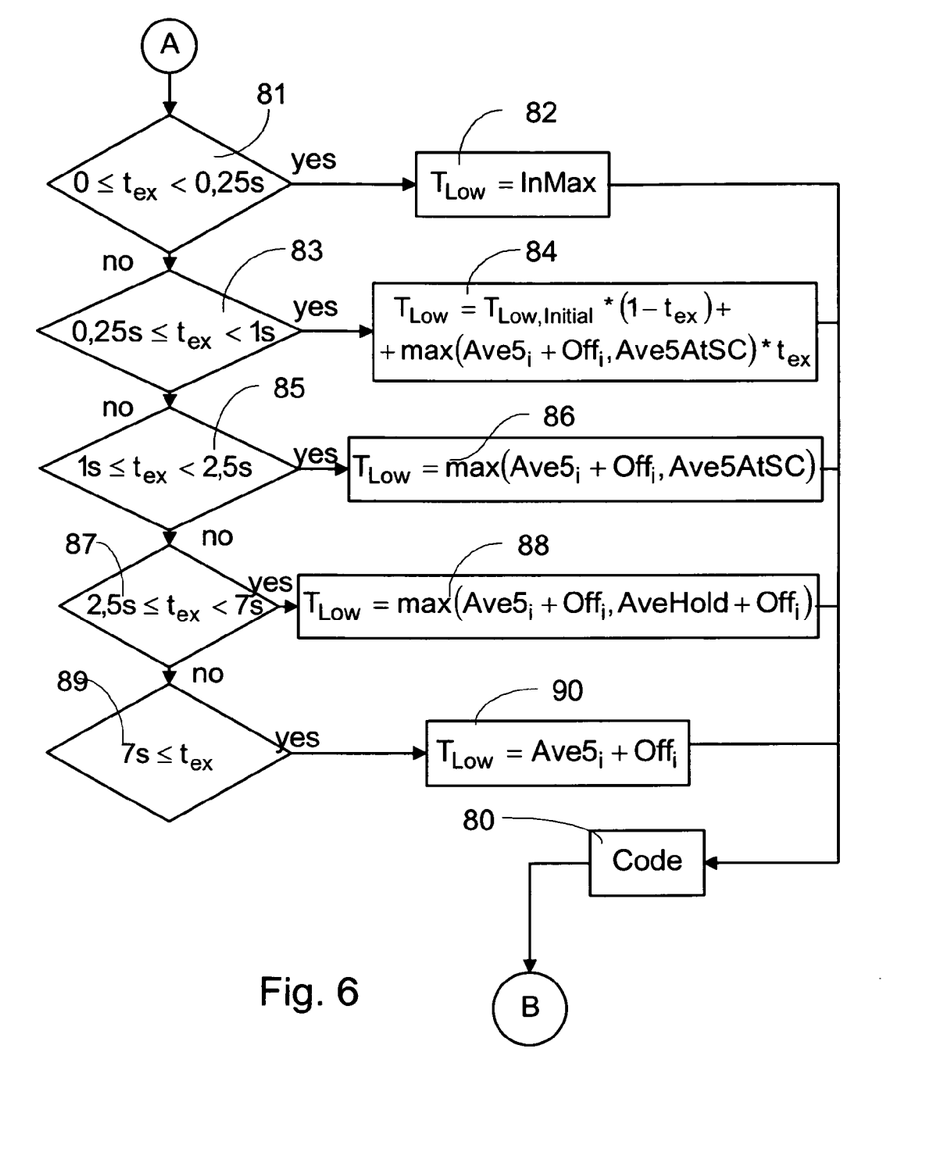
Figure 7:
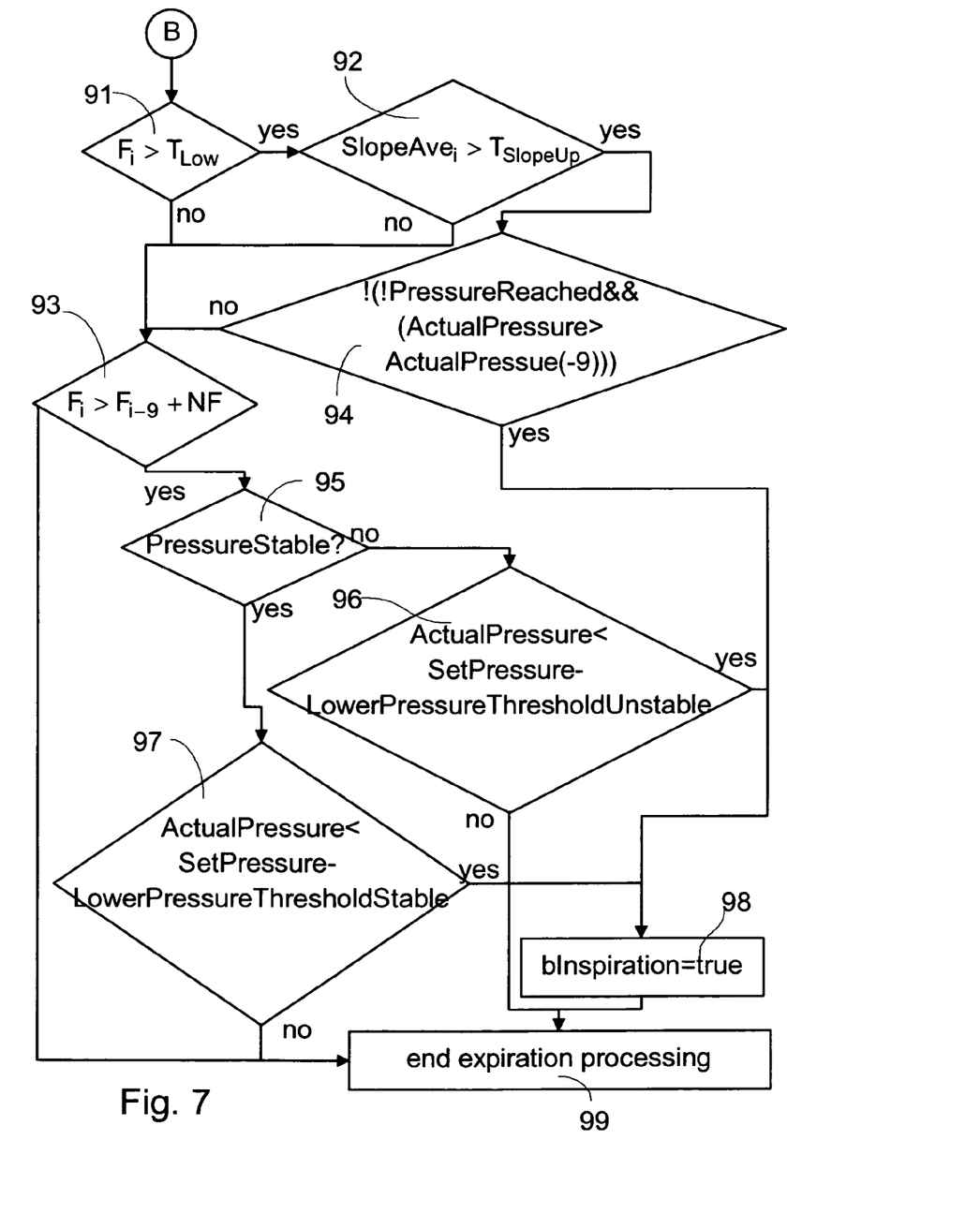

The expiration processing in step 57 is explained by means of FIGS. 5 to 7.

In step 72, a so-called offset Off$_i$ is calculated for each index i according to formula (7):

$$Off_i = (HighAve_i - Ave5[00]_i)/6 \qquad (7)$$

In another embodiment, the Offset Off$_i$ may be calculated according to formula (7') in step 72.

$$Off_i = (HighAve_i - LowAve_i)/10 \qquad (7')$$

Next, in step 78, the memory AveHold=Ave1$_i$ is set for three seconds, if $t_{ex}>1$ s and $F_i>Ave5_i$ and $F_i=Ave1_i$. The latter three conditions are verified in steps 73 to 75. From this follows that also Ave1$_i>$Ave5$_i$. $t_{ex}$ here stands for the time since the last switching to the expiration mode. The time at which AveHold=Ave1$_i$ is set is stored in memory $t_{AH0}$ (AH=AveHold) in step 79. If one of the conditions verified in steps 73 to 75 is not fulfilled, it is verified in step 76 whether the three seconds have already expired. If so, memory AveHold=0 is set in step 77.

In another embodiment, it is additionally examined as to whether memory AveHold=0, before AveHold is set. This causes memory AveHold to remain unchanged after being set.

In another embodiment AveHold will be reset, i.e. set to 0, when switching to the inspiration mode.

In FIG. 6 it is explained how the expiration threshold value $T_{LOW}$ designated with reference numeral 3 in FIG. 1 is obtained. In steps 81,83, 85,87 and 89, the time since the last switching to the expiration mode $t_{ex}$ is divided into five domains designated with reference numerals 14, 15, 16, 17 and 18 in FIG. 1. In the first domain, if $0 \le t_{ex}<0.25$ s, the expiration threshold value $T_{LOW}$ according to formula (8) is set equal to the maximum of the airflow during the preceding inspiration phase InMax, which is designated with reference numeral 8 in FIG. 1. This practically prevents a switching to the inspiration mode during the first 0.25 s.

$$T_{Low} = \text{InMax wenn} \, 0 \le t_{ex} < 0.25 \text{ s} \qquad (8)$$

If 0.25 s$<t_{ex}<1$ s the expiration threshold value $T_{Low}$ is lowered during the time span 15 approximately linearly with time according to formula (9). Ave5AtSC is equal to Ave5$_i$ with $t_{ex}=0$, i.e. at the moment of switching from the inspiration mode to the expiration mode. The function max (x,y) returns x, if x>y and otherwise y.

$$T_{Low} = T_{Low,Initial} * (1-t_{ex}) + \max(Ave5_i + Off_i, Ave5AtSC) \\ * t_{ex} \qquad (9)$$

if 0.25s$\le t_{ex}<1$ s

Next, in steps 86, 88 and 90, the expiration threshold value $T_{Low}$ is calculated for the time segments 16, 17 and 18 in accordance with the following formulae 10 to 12.

$$T_{Low} = \max(Ave5_i + Off_i, Ave5AtSC) \text{ if } 1s \le t_{ex}<2.5 \text{ s} \qquad (10)$$

$$T_{Low} = \max(Ave5_i + Off_i, AveHold + Off) \text{ if } 2.5s \le t_{ex}<7 \text{ s} \qquad (11)$$

$$T_{Low} = Ave5_i + Off_i \text{ if } 7 \text{ s} \le t_{ex} \qquad (12)$$

Apart from the expiration threshold value $T_{Low}$ it will be determined according to the following C or JavaScript Code (compare JavaScript Das umfassende Referenzwerk, David Flanagan, Translator Ralf Kuhnert et al., O'Reilly, Köln, ISBN 3-930673-56-8) whether the set pressure SetPressure predefined by parts of the software has already been reached and the actual pressure measured by the pressure sensor 36 remains stable on the set pressure. The code line numbers on the right-hand edge of the page are not part of the code, but merely serve reference purposes. In step 80, the following code is run through every 10 ms.

Even though the set pressure SetPressure is reduced stepwise when switching from the inspiration mode to the expiration mode, the actual pressure ActualPressure remains initially unchanged and is then gradually reduced to the new set pressure. During this phase the variable PressureReached=0. After the checking !PressureReached in code line 1, where PressureReached is inverted by "!", it is checked in this phase in code line 2 whether ActualPressure<=SetPressure, which is not the case as yet. ActualPressure has dropped to or below SetPressure only in a later code run. Now, PressureReached is incremented in code line 2, i.e. =1 is set. In the next code run, after the checking in code line 1, PressureReached is incremented in code line 4. Then, the inverted variable PressureStable is verfied in code line 5. PressureStable is initially 0. Therefore, it is subsequently verified in code line 6 whether ActualPressure>=SetPressure. If the actual pressure ActualPressure overshoots below SetPressure, this condition is not fulfilled till the end of the overshoot. In the next code run, the condition !PressureStable is no longer fulfilled, so that code line 6 is skipped. PressureReached and PressureStable are further incremented in the following code runs until the condition ActualPressure>SetPressure+LowerPressureThreshold Stable in code line 7 is fulfilled. LowerPressureThresholdStable here is a predetermined value in the range from 0.5 to 1 mbar. This may happen either with a second overshoot where the actual pressure again rises by LowerPressureThreshold Stable above the set pressure. A second possibility is coughing or sneezing. The pressure fluctuations then occurring are too fast for the pressure controlling of the bi-level apparatus, so that they are not adjusted. The variable PressureStable is evaluated in step 95 as to prevent a switching to the inspiration mode in the event of coughing or sneezing.

```
if (!PressureReached)                                                    1
    { if (Actual Pressure<=SetPressure) PressureReached ++; }            2
else {                                                                   3
    PressureReached ++;                                                  4
    if (!PressureStable)                                                 5
        { if (ActualPressure>=SetPressure) PressureStable++; }           6
    else if                                                              7
    (ActualPressure>SetPressure+LowerPressureThresholdStable)
        { PressureReached =0; PressureStable=0; }                        8
    else PressureStable++;                                               9
    }                                                                   10
```

One of the following three conditions must be fulfilled to allow the switching from the expiration mode to the inspiration mode:
1) if $F_i > T_{Low}$ && $SlopeAve_i > T_{SlopeUp}$ && (!PressureReached && (ActualPressure>ActualPressure(−9))) or
2) if ActualPressure<SetPressure−LowerPressureThresholdUnstable && $F_i > F_{i-9} + NF$ or
3) if PressureStable && ActualPressure<SetPressure−LowerPressureThresholdStable && $F_i > F_{i-9} + NF$.

These conditions are also shown in the flowchart of FIG. 7. The usual case for the switching to the inspiration mode is that the conditions are fulfilled in steps 91 and 92, i.e. that the airflow $F_i$ is greater than the expiration threshold value $T_{Low}$ and the derivative $SlopeAve_i$ is greater than the expiration derivative threshold value $T_{SlopeUp}$. The condition (!PressureReached && (ActualPressure>ActualPressure(−9))) verified in step 94 prevents a switching to the inspiration mode in the event of coughing or sneezing. In the event of coughing the actual pressure rises above the set pressure for a short period. Here, PressureReached=0 is set in code line 8. ActualPressure(−9) designates the actual pressure 90 ms ago. −9 is an offset relating to the current index. The 90 ms then result from the measurement of an actual pressure every 10 ms. The comparison between the current actual pressure and the actual pressure 90 ms ago shows whether a pressure increase has indeed taken place.

The conditions 2 and 3 are structured similarly and are verified in steps 93 and 95 to 97. According to these conditions a switching to the inspiration mode takes place if the airflow is increased ($F_i > F_{i-9} + NF$) when the patient takes a deep breath and the actual pressure simultaneously drops below the set pressure. In dependence on the variable PressureStable a differently high drop of the actual pressure below the set pressure is required in steps 96 and 97. LowerPressureThresholdUnstable and LowerPressureThresholdStable are predetermined constants.

Figure 8:
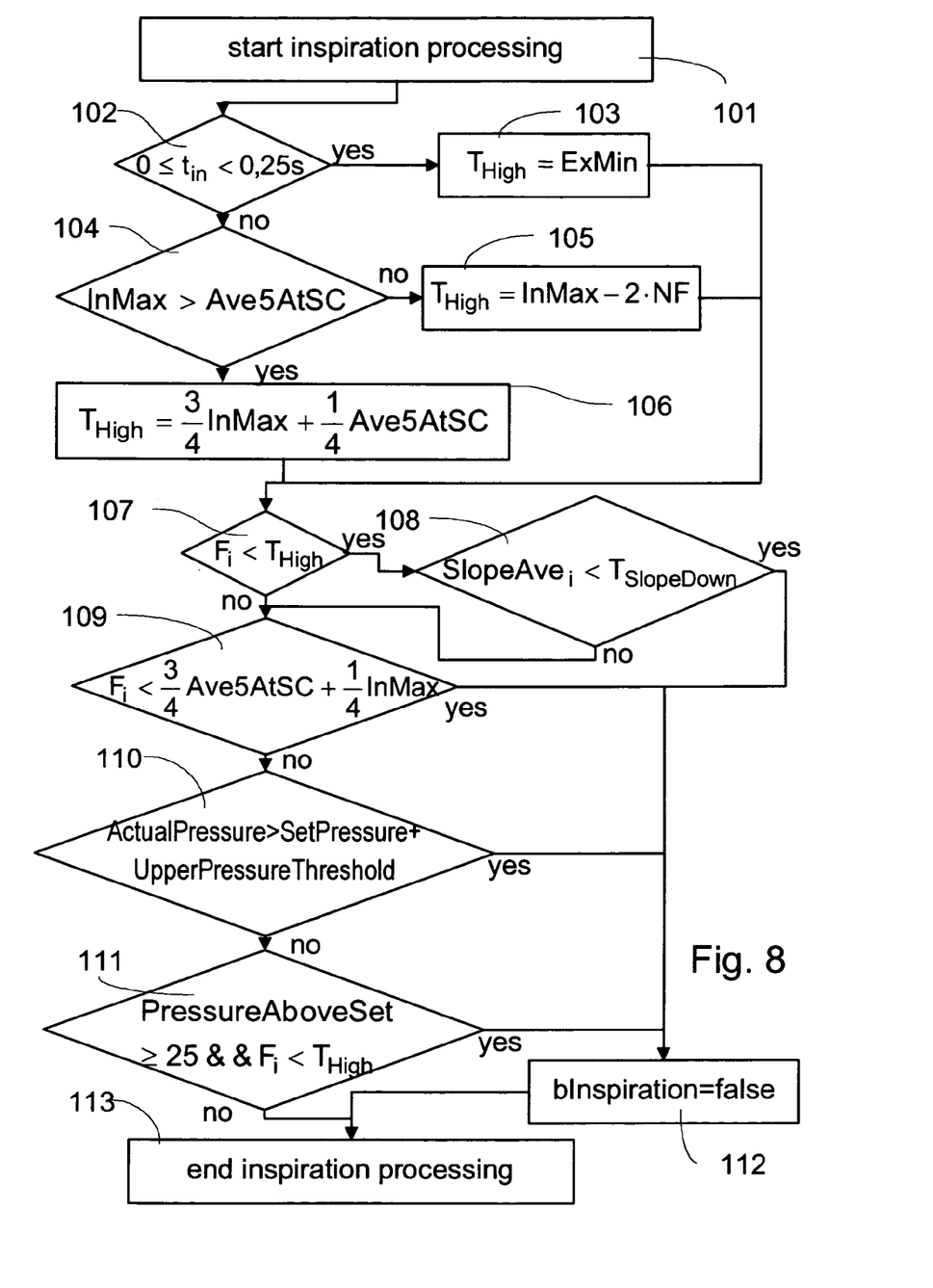
FIG. 8 shows a detailed flowchart for the inspiration processing.

The inspiration processing shown in FIG. 8 is less complicated. A distinction is made only between two time domains for time $t_{in}$ since the last switching to the inspiration mode, namely 0 to 0.25 s and later than 0.25 s in step 102. Within 0.25 s after the switching to the inspiration mode the inspiration threshold value $T_{High}$, reference numeral 4, is set according to formula (13) equal to the minimum of the airflow during the preceding expiration phase ExMin 7. This practically prevents a return to the expiration mode within the first 0.25 seconds.

$$T_{High} = \text{ExMinif0} \le t_{in} \le 0.25 \text{ s} \qquad (13)$$

Upon the expiration of the first 0.25 seconds it is verified in step 104 whether the previous maximum airflow is greater during the current inspiration phase InMax than Ave5AtSC. Ave5AtSC is the moving average value over 500 measured airflow values at the time of the preceding switching from the expiration mode to the inspiration mode. If this is the case, the inspiration threshold value $T_{High}$ is calculated in step 106 according to formula (14). Otherwise, the inspiration threshold value $T_{High}$ is calculated in step 105 according to formula (15).

$$T_{High} = \frac{3}{4}\text{InMax} + \frac{1}{4}Ave5AtSC \text{ if } \text{InMax} > Ave5AtSC \qquad (14)$$

$$T_{High} = \text{InMax} - 2NF \text{ if } \text{InMax} \le Ave5AtSC \qquad (15)$$

The reference numerals 20, 21, 22 and 23 in FIG. 1 relate to the time segments during an inspiration phase which are separated by two local and one absolute maximum of the airflow $F_i$. The inspiration threshold value $T_{High}$ is shifted further up with every exceeded maximum. Normally InMax>Ave5AtSC so that formula (14) is applied. The inspiration phase shown left in FIG. 1 is less interesting. Here, the inspiration threshold value $T_{High}$ is increased more and more prior to reaching the maximum 8 of the airflow in time segment 12 and remains constant after having exceeded the maximum 8 in time segment 13.

Next, prior to the decision in step 107, the following C Code is executed. Like the rest of the inspiration processing, also the code is run through every 10 ms. The code lines 11 to 20 correspond to the above code lines 1 to 10. It must be considered, however, that the set pressure SetPressure is increased stepwise during the transition into the inspiration phase, so that the actual pressure approximates the set pressure from below at the beginning of the inspiration phase.

This has the consequence that the relational operators ">" and "<" are currently interchanged.

In code lines 21 to 23 it is measured how long the actual pressure was above the set pressure. In the variable Pressure-AboveSet the time is counted up. The value of Pressure-AboveSet must be multiplied by 10 ms to actually obtain the time.

```
if (!PressureReached)                                              11
    { if (ActualPressure>=SetPressure) PressureReached ++; }       12
else    {                                                          13
    PressureReached ++;                                            14
    if (!PressureStable)                                           15
        { if (ActualPressure<=SetPressure) PressureStable++; }     16
    else if (ActualPressure<SetPressure-UpperPressureThreshold)    17
        { PressureReached =0; PressureStable=0; }                  18
    else PressureStable ++;                                        19
    }                                                              20
if (PressureStable && (ActualPressure>SetPressure))                21
    PressureAboveSet++;                                            22
else PressureAboveSet =0;                                          23
```

One of the following four conditions must be fulfilled to allow the switching from the inspiration mode to the expiration mode:

1) if $F_i < T_{High}$ && $SlopeAve_i < T_{SlopeDown}$ or 2) if $F_i < \frac{3}{4} Ave5AtSC + \frac{1}{4} \ln Max$ or 3) if ActualPressure>SetPressure+UpperPressureThreshold or 4) if PressureAboveSet≧25 && $F_i < T_{High}$ The usual case for the switching to the expiration mode is that the conditions are fulfilled in steps 107 and 108, i.e. that the airflow $F_i$ is smaller than the inspiration threshold value $T_{High}$ and the derivative $SlopeAve_i$ is smaller than the inspiration derivative threshold value $T_{SlopeDown}$.

The second condition, which is verified in step 109, merely concentrates on whether the airflow $F_i$ drops below a predetermined threshold.

Moreover, switching to the expiration mode takes place in accordance with the third condition if the actual pressure increases by UpperPressureThreshold above the set pressure. This condition is verified in step 110.

Finally, in accordance with the fourth condition, the switching to the expiration mode takes place if the actual pressure is above the set pressure for more than 0.25 s and the airflow $F_i$ simultaneously drops below the inspiration threshold value $T_{High}$, which is verified in step 111.

During the switching to expiration the Boolean variable bInspiration is set to false in step 112.

The invention was explained in more detail by means of preferred embodiments above. A person skilled in the art will appreciate, however, that various alterations and modifications may be made without departing from the gist of the invention. Therefore, the scope of protection will be defined by the hereinafter following claims and their equivalents.

What is claimed is:

1. A method for controlling a bi-level apparatus, comprising: using a flow sensor to repeatedly measure an airflow thereby obtaining measured airflow values; choosing an expiration threshold value; choosing an inspiration threshold value; using a processor to repeatedly compare said airflow values with said expiration threshold value during an expiration mode; switching to an inspiration mode if an airflow value is greater than said expiration threshold value in a comparison with said expiration threshold value; using the processor to repeatedly compare said airflow values with said inspiration threshold value during said inspiration mode; and using the processor to switch to said expiration mode if the airflow value is smaller than said inspiration threshold value in a comparison with said inspiration threshold value, wherein the processor performs the steps of: storing a minimum airflow during said expiration mode; choosing said inspiration threshold value equal to said stored minimum airflow immediately after switching to said inspiration mode; storing a maximum airflow during said inspiration mode; and choosing said expiration threshold value equal to said stored maximum airflow immediately after switching to said expiration mode, wherein during a time span shortly after said switching to said inspiration mode up to the end of said inspiration mode, said inspiration threshold value is chosen by the processor to be equal to a difference of a maximum of said airflow during said current inspiration phase minus a predetermined value.

2. The method according to claim 1, the processor performing the steps of: calculating an airflow derivative by estimating a time derivative of said airflow; comparing said airflow derivative with an expiration derivative threshold value during the expiration mode; switching to said inspiration mode only if additionally said airflow derivative is greater than said expiration derivative threshold value; comparing said airflow derivative with an inspiration derivative threshold value during the inspiration mode; switching to said expiration mode only if additionally said airflow derivative is less than said inspiration derivative threshold value.

3. The method according to claim 2, wherein said calculating said airflow derivative includes: repeatedly calculating a median from a first predetermined number of successive measured airflow values; calculating an averaged airflow as arithmetic average of a second given number of median values; and calculating said time derivative of said averaged airflow to obtain said airflow derivative.

4. The method according to claim 2, wherein said airflow derivative is averaged over a first predetermined time span by the processor prior to said comparison with said expiration and inspiration derivative threshold value.

5. The method according to claim 1, wherein no switching from said expiration mode to said inspiration mode by the processor takes place if an actual pressure is not a set pressure and a current actual pressure is above the actual pressure measured before a given time span prior to a current time.

6. The method according to claim 1, wherein switching from said expiration mode to said inspiration mode by the processor takes place if an actual pressure is below a set pressure by a first given value and a current airflow is above an airflow preceding a given time span prior to a current time by a second given value.

7. The method according to claim 1, the processor performing the steps of: calculating a first moving average value by a first predetermined number of measured airflow values measured exclusively during an expiration mode, said first predetermined number of measured airflow values being consecutive; calculating a second moving average value by a second predetermined number of measured airflow values measured exclusively during the inspiration mode, said second predetermined number of measured airflow values being consecutive.

8. The method according to claim 7, the processor performing the steps of: lowering said expiration threshold value during a first time span shortly after switching to said expiration mode from a maximum airflow measured during the preceding inspiration phase to a first sum of said first moving average value weighted by a first factor plus said second moving average value weighted by a second factor, wherein said first factor is slightly smaller than one and a second sum of said first and second factor is equal to one; and choosing said expiration threshold value equal to said first sum following said first time span.

9. The method according to claim 8, wherein said expiration threshold value is only lowered by the processor to a switching average value during said first time span if said switching average value is greater than said first sum, and said expiration threshold value is chosen by the processor to be equal to said switching average value during a second time span following said first time span if said switching average value is greater than said first sum, wherein said switching average value is equal to said first moving average value at the moment of the preceding switching to said expiration mode.

10. The method according to claim 9, wherein during the time span shortly after said switching to said inspiration mode up to the end of said inspiration mode, said inspiration threshold value is chosen by the processor to be equal to said maximum of said airflow during a current inspiration phase multiplied by said first factor minus said switching average value multiplied by said second factor, wherein said first factor is slightly smaller than one and a sum of said first factor plus said second factor is equal to one.

11. The method according to claim 7, the processor performing the steps of: calculating a third moving average value over a predetermined number of consecutively measured airflow values; storing said third moving average value during a first time span for a second time span being shorter than said first time span in a memory if both said airflow and said third moving average value are greater than said first moving average value and said airflow is equal to said third moving average value; otherwise storing of zero in said memory; calculating a difference of said second moving average value minus said first moving average value; multiplying said difference by a first factor to obtain a product; and adding said product to said value in said memory to obtain said expiration threshold value.

12. The method according to claim 1, wherein during the time span shortly after said switching to said inspiration mode up to the end of said inspiration mode, said inspiration threshold value is chosen by the processor to be equal to said maximum of said airflow during a current inspiration phase multiplied by a first factor minus a switching average value multiplied by a second factor, wherein said first factor is slightly smaller than one and a sum of said first factor plus said second factor is equal to one, provided that said maximum of said airflow during said current inspiration phase is greater than said switching average value, while otherwise said inspiration threshold value during the time span is chosen to be equal to a difference of said maximum of said airflow during said current inspiration phase minus the predetermined value.

13. A respiratory apparatus, comprising: a fan; a pressure sensor for determining an overpressure under which air is provided by said fan; a flow sensor for measuring an airflow; a processor connected to said pressure sensor and said flow sensor, to which a pressure signal is fed from said pressure sensor and an airflow signal from said flow sensor, said processor storing a sequence of instructions and being suitable for executing said instructions, said processor performing the following when executing said instructions: repeatedly obtaining measured airflow values from said airflow signal; choosing an expiration threshold value; choosing an inspiration threshold value; repeatedly comparing said airflow values with said expiration threshold value during an expiration mode; switching to an inspiration mode if an airflow value is greater than said expiration threshold value in a comparison with said expiration threshold value; repeatedly comparing said airflow values with said inspiration threshold value during said inspiration mode; and switching to said expiration mode if the airflow value is smaller than said inspiration threshold value in a comparison with said inspiration threshold value, wherein the processor is adapted for storing a minimum airflow during said expiration mode; choosing said inspiration threshold value equal to said stored minimum airflow immediately after switching to said inspiration mode; storing a maximum airflow during said inspiration mode; and choosing said expiration threshold value equal to said stored maximum airflow immediately after switching to said expiration mode, wherein during a time span shortly after said switching to said inspiration mode up to the end of said inspiration mode, said inspiration threshold value is chosen to be equal to a difference of a maximum of said airflow during said current inspiration phase minus a predetermined value.

14. The respiratory apparatus according to claim 13, said processor further performing the following during operation: calculating an airflow derivative by estimating a time derivative of said airflow; comparing said airflow derivative with an expiration derivative threshold value during the expiration mode; switching to said inspiration mode only if additionally said airflow derivative is greater than said expiration derivative threshold value; comparing said airflow derivative with an inspiration derivative threshold value during the inspiration mode; switching to said expiration mode only if additionally said airflow derivative is less than said inspiration derivative threshold value.

15. The respiratory apparatus according to claim 14, wherein said calculating said airflow derivative includes: repeatedly calculating a median from a first predetermined number of successive measured airflow values thereby obtaining median values; calculating an averaged airflow as arithmetic average of a second given number of median values; and calculating said time derivative of said averaged airflow to obtain said airflow derivative.

16. The respiratory apparatus according to claim 14, wherein said processor further averaging said airflow derivative over a first predetermined time span prior to said comparison with said expiration and inspiration derivative threshold value.

17. The respiratory apparatus according to claim 13, wherein no switching from said expiration mode to said inspiration mode takes place if an actual pressure is not yet settled on a set pressure and a current actual pressure is above an actual pressure measured before a given time span prior to a current time.

18. The respiratory apparatus according to claim 13, wherein switching from said expiration mode to said inspiration mode takes place if an actual pressure is below a set pressure by a first given value and a current airflow is above an airflow preceding a given time span prior to a current time by a second given value.

19. The respiratory apparatus according to claim 13, said processor further performing the following when executing said instructions: calculating a first moving average value by a first predetermined number of airflow values measured exclusively during the expiration mode, said first predetermined number of measured airflow values being consecutive; calculating a second moving average value by a second predetermined number of measured airflow values measured exclusively during the inspiration mode, said second predetermined number of measured airflow values being consecutive.

20. The respiratory apparatus according to claim 19, said processor further performing the following when executing said instructions: lowering said expiration threshold value during a first time span after switching to said expiration mode from a maximum airflow measured during the preceding inspiration phase to a first sum of said first moving average value weighted by a first factor plus said second moving average value weighted by a second factor, wherein said first factor is slightly smaller than one and a second sum of said first and second factor is equal to one; and choosing said expiration threshold value equal to said first sum following said first time span.

21. The respiratory apparatus according to claim 20, wherein the expiration threshold value is only lowered to a switching average value during said first time span if said switching average value is greater than said first sum, and said expiration threshold value is chosen to be equal to said switching average value during a second time span following said first time span if said switching average value is greater than said first sum, wherein said switching average value is equal to said first moving average value at the moment of the preceding switching to said expiration mode.

22. The respiratory apparatus according to claim 19, said processor further performing the following when executing said instructions: calculating a third moving average value over a third predetermined number of measured airflow values; storing said third moving average value during a first time span for a second time span being shorter than said first time span in a memory if both said airflow and said third moving average value are greater than said first moving average value and said airflow is equal to said third moving average value; otherwise storing of zero in said memory; calculating a difference of said second moving average value minus said first moving average value; multiplying said difference by a factor to obtain a product; and adding said product to said value in said memory to obtain said expiration threshold value.

23. The respiratory apparatus according to claim 13, wherein during the time span shortly after said switching to said inspiration mode up to the end of said inspiration mode, said inspiration threshold value is chosen to be equal to said maximum of said airflow during a current inspiration phase multiplied by a first factor minus said switching average value multiplied by a second factor, wherein said first factor is slightly smaller than one and a sum of said first factor plus said second factor is equal to one.

24. The respiratory apparatus according to claim 13, wherein during the time span shortly after said switching to said inspiration mode up to the end of said inspiration mode, said inspiration threshold value is chosen to be equal to said maximum of said airflow during a current inspiration phase multiplied by a first factor minus a switching average value multiplied by a second factor, wherein said first factor is slightly smaller than one and a sum of said first factor plus said second factor is equal to one, provided that said maximum of said airflow during said current inspiration phase is greater than said switching average value, while otherwise said inspiration threshold value during the time span is chosen to be equal to a difference of said maximum of said airflow during said current inspiration phase minus the predetermined value.

25. A respiratory apparatus, comprising: a fan; a pressure sensor for determining an overpressure under which air is provided by said fan; a flow sensor for measuring an airflow; and means for processing a pressure signal from said pressure sensor and an airflow signal from said flow sensor, said processing means repeatedly obtaining measured airflow values from said airflow signal; choosing an expiration threshold value; choosing an inspiration threshold value; repeatedly comparing said airflow values with said expiration threshold value during an expiration mode; switching to an inspiration mode if an airflow value is greater than said expiration threshold value in a comparison with said expiration threshold value; repeatedly comparing said airflow values with said inspiration threshold value during said inspiration mode; and switching to said expiration mode if the airflow value is smaller than said inspiration threshold value in a comparison with said inspiration threshold value, wherein the processing means is adapted for storing a minimum airflow during said expiration mode; choosing said inspiration threshold value equal to said stored minimum airflow immediately after switching to said inspiration mode; storing a maximum airflow during said inspiration mode; and choosing said expiration threshold value equal to said stored maximum airflow immediately after switching to said expiration mode, wherein during a time span shortly after said switching to said inspiration mode up to the end of said inspiration mode, said inspiration threshold value is chosen to be equal to a difference of a maximum of said airflow during said current inspiration phase minus a predetermined value.

* * * * *